(12) United States Patent
Aven

(10) Patent No.: US 6,566,308 B1
(45) Date of Patent: May 20, 2003

(54) EMULSIFIABLE CONCENTRATE CONTAINING ONE OR MORE PESTICIDES AND ADJUVANTS

(75) Inventor: Michael Aven, Mainz (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/466,747

(22) Filed: Dec. 17, 1999

Related U.S. Application Data

(60) Provisional application No. 60/117,707, filed on Jan. 29, 1999.

(51) Int. Cl.[7] ................................................. A01N 25/30
(52) U.S. Cl. ..................... 504/347; 504/363; 514/237.5; 514/687; 514/937
(58) Field of Search ................................. 504/363, 347; 514/237.5, 687, 937

(56) References Cited

U.S. PATENT DOCUMENTS

| 5,374,603 A | * | 12/1994 | Mulqueen et al. | ........... 504/130 |
| 5,385,948 A | | 1/1995 | Chaudhuri et al. | ........... 514/788 |
| 5,679,866 A | | 10/1997 | Curtze et al. | ............... 568/333 |
| 5,731,264 A | * | 3/1998 | Narayanan et al. | ........... 504/116 |
| 5,834,400 A | | 11/1998 | Narayanan et al. | ........... 504/116 |

FOREIGN PATENT DOCUMENTS

| EP | 0143099 | 5/1985 | .......... A01N/25/04 |
| EP | 0933025 | 8/1999 | .......... A01N/25/02 |
| EP | 1023837 | 8/2000 | .......... A01N/43/50 |
| EP | 1025757 | 8/2000 | .......... A01N/25/02 |
| WO | WO 98/00008 | 1/1998 | |
| WO | WO 98/48624 | 11/1998 | |
| WO | 0101777 | 1/2001 | .......... A01N/25/02 |

* cited by examiner

Primary Examiner—S. Mark Clardy
(74) Attorney, Agent, or Firm—Charles F. Costello

(57) ABSTRACT

The invention relates to a stable emulsifiable concentrate (EC) for crop protection active compounds which comprises (a) one or more crop protection active compounds,
(b) 150 to 500 g/l of one or more adjuvants,
(c) optionally one or more organic, non-polar solvents,
(d) an emulsifying surfactant system forming an oil in water emulsion when the formulation is added to water, which essentially consists of
one or more non-ionic surfactants, and
one or more anionic surfactants,
(e) a water-miscible polar aprotic solvent or one or more dimethyl dicarboxylates, and
(f) optionally an antifoam agent, and to the use of such a suspension as a pesticide.

13 Claims, No Drawings

EMULSIFIABLE CONCENTRATE CONTAINING ONE OR MORE PESTICIDES AND ADJUVANTS

This application claims priority from copending provisional application(s) Ser. No. 60/117,707 filed on Jan. 29, 1999.

BACKGROUND OF THE INVENTION

Emulsifiable concentrate (EC) formulations conventionally contain an active ingredient, one or more surfactants which act as emulsifiers upon dilution of the EC with water and a water immiscible solvent. Typical solvents for conventional EC formulations are aromatic hydrocarbons as for example xylene, Shellsol A or Solvesso 200. These solvents have very low solubilities in water and a high capability of dissolving a wide range of active ingredients.

Due to the presence of the solvent, many pesticides formulated as an EC have advantages such as a higher degree of systemicity and higher overall activity compared to the same pesticide formulated as a wettable powder (WP), water dispersible granule (WG) or suspension concentrate (SC).

The observed efficacy of the combination of ingredients can sometimes be significantly higher than would be expected from the amounts of the individual ingredients used (synergism). The efficacy of the active components can often be improved by addition of other ingredients such as adjuvants.

In view of increasing the ease and safety of handling and dosing of these adjuvants by the end-user and in view of avoiding unnecessary packaging material, it is desirable to develop concentrated formulations which already contain such adjuvants.

The International Patent Application WO 98/00008 discloses EC formulations containing one or more pesticides, three different kinds of non-ionic surfactants, one of which is a tristyrenephenol ethoxylate, a water-miscible cosolvent and a water-immiscible solvent. However, there is no suggestion of EC formulations containing a pesticidal compound, an adjuvant and an anionic surfactant. Since no defoaming agent is used, it is likely that foaming would be a major problem with the dilutions of the described recipes.

SUMMARY OF THE INVENTION

The present invention provides a novel stable emulsifiable concentrate (EC) formulation for crop protection active compounds which comprises
(a) one or more crop protection active compounds;
(b) 150 to 500 g/l of one or more adjuvants;
(c) optionally one or more organic solvents;
(d) an emulsifying surfactant system enabling an oil in water emulsion to be formed when the formulation is added to water, which comprises
one or more non-ionic surfactants, and
one or more anionic surfactants,
(e) a water-miscible polar aprotic solvent, or one or more dimethyl dicarboxylates, and
(f) optionally one or more antifoam agents.

An adjuvant is defined here as a substance which can increase the biological activity of an active ingredient but is not itself significantly biologically active. An adjuvant can either be included in the formulation or can be added to the spray tank together with the formulation containing the active ingredient.

The new EC shows excellent selective pesticidal activity in various crops.

It is an object of the present invention to provide novel, pesticidal ECs.

It is also an object of the invention to provide methods for controlling pests by contacting plants with a pesticidally effective amount of the new EC.

It is another object of the invention to provide selective pesticidal compositions obtainable by emulsifying the new ECs in water.

These and other objects and features of the invention will be more apparent from the detailed description set forth hereinbelow, and from the appended claims.

DETAILED DESCRIPTION OF THE PREFERRED EMBODIMENTS

It has surprisingly been found that improved stable EC formulations containing one or more pesticidal active ingredients and at least 150 g of one or more adjuvants can be produced using
optionally one or more organic solvents,
an emulsifying surfactant system enabling an oil in water emulsion to be formed when the formulation is added to water, which comprises one or more non-ionic surfactants and one or more anionic surfactants,
a co-solvent selected from the class of water-miscible polar aprotic solvents, or one or more dimethyl dicarboxylates, and
optionally one or more antifoam agents.

The use of a water-miscible polar aprotic solvent, in particular γ-butyrolactone, is essential to incorporate sufficient amounts of the pesticidal active ingredient and the adjuvant into the EC.

In the definitions of the new EC formulations, a pesticide is a synthetic or natural compound which has the capability of inhibiting the growth of phytopathogenic fungi or of controlling a plant disease or has the capability to control undesired weeds or insects in crops. Preferably, the pesticide is selected from the group consisting of herbicides, insecticides, fungicides, bactericides, nematicides, algicides, molluscicides, rodenticides, virucides, compounds inducing resistance into plants, biological control agents such as viruses, bacteria, nematodes, fungi and other microorganisms, repellents of birds and animals, and plant growth regulators, or mixtures thereof.

Suitable pesticides are those which are substantially insoluble in water, but soluble in an organic solvent.

The new ECs contain at least one pesticide, preferably one, two or three pesticides, in particular fungicides, herbicides or insecticides.

The fungicidal compounds can be, for example, those which are capable of combating ear diseases of cereals (e.g. wheat) such as Septoria, Gibberella and Helminthosporium spp., seed and soil borne diseases, downy and powdery mildews on vines, and powdery mildew and scab on apples, etc. Mixtures of fungicidal compounds can have a broader spectrum of activity than a single compound alone. Furthermore, the mixtures of fungicides can exhibit a synergistic effect compared with the single active ingredients.

Preferred fungicides are water-insoluble compounds selected from the group consisting of:

AC 382042, anilazine, azoxystrobin, benalaxyl, benomyl, binapacryl, bitertanol, blasticidin S, Bordeaux mixture, bromuconazole, bupirimate, captafol, captan, carbendazim, carboxin, carpropamid, chlorbenzthiazon, chlorothalonil, chlozolinate, cycloheximide, cymoxanil, cypofuram, cyproconazole, cyprodinil, dichlofluanid, dichlone, dichloran, diclobutrazol, diclocymet, diclomezine, diethofencarb, difenoconazole, diflumetorim, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenamidone, fenarimol, fenbuconazole, fenfuram, fenhexamid, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetyl-aluminium, fuberidazole, furalaxyl, furametpyr, guazatine, hexaconazole, IKF-916, imazalil, iminoctadine, ipconazole, iprodione, isoprothiolane, iprovalicarb, kasugamycin, KH-7281, kitazin P, kresoxim-methyl, mancozeb, maneb, mepanipyrim, mepronil, metalaxyl, metconazole, methfuroxam, MON 65500, myclobutanil, neoasozin, nickel dimethyldithiocarbamate, nitrothalisopropyl, nuarimol, ofurace, organo mercury compounds, oxadixyl, oxycarboxin, penconazole, pencycuron, phenazineoxide, phthalide, polyoxin D, polyram, probenazole, prochloraz, procymidione, propamocarb, propiconazole, propineb, pyrazophos, pyrifenox, pyrimethanil, pyroquilon, pyroxyfur, quinomethionate, quinoxyfen, quintozene, spiroxamine, SSF-126, SSF-129, streptomycin, sulfur, tebuconazole, tecloftalame, tecnazene, tetraconazole, thiabendazole, thifluzamide, thiophanate-methyl, thiram, tolclofosmethyl, tolylfluanid, triadimefon, triadimenol, triazbutil, triazoxide, tricyclazole, tridemorph, trifloxystrobin, triflumizole, triforine, triticonazole, validamycin A, vinclozolin, XRD-563, zarilamid, zineb, ziram, and in particular dimethomorph, metconazole, triadimenol or prochloraz.

Moreover, the EC formulations according to the invention may contain a chemical agent that induces the systemic acquired resistance in plants such as for example isonicotinic acid or derivatives thereof, 2,2-dichloro-3,3-dimethylcyclopropane carboxylic acid or BION.

These fungicidal compounds are mostly known from "The Pesticide Manual", 11th Edition, The British Crop Protection Council and The Royal Society of Chemistry, 1997, (hereinbelow abbreviated as "Pesticide Manual").

Another group of preferred fungicidal compounds are the benzoylbenzenes disclosed by EP-A-0 727 141, in particular those of formula I

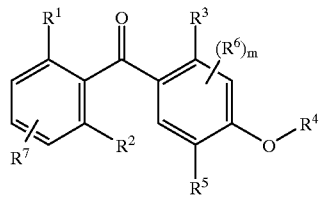

wherein
$R^1$ represents a chloro atom or a methyl or trifluoromethyl group;
$R^2$ represents a chloro atom or an alkyl, alkoxy or hydroxy group;
$R^3$ represents a halogen atom, an optionally substituted alkyl, alkoxy, alkenyl, alkylthio, alkylsulfinyl, alkylsulfonyl, cyano, carboxy, hydroxy, nitro or an optionally substituted amino group;
$R^4$ represents an optionally substituted alkyl group;
$R^5$ represents an optionally substituted alkyl, alkoxy, alkenyloxy, alkynyloxy, alkylthio, cycloalkyl, cycloalkyloxy, group;

m is an integer of 1 or 2;
$R^6$ independently represents an optionally substituted alkoxy or alkanoyloxy group; and
$R^7$ represents a hydrogen or halogen atom or an alkyl, haloalkyl or alkoxy group.

Particularly preferred is 5-bromo-2',6-dimethyl-2,4',5',6'-tetramethoxymethoxybenzophenone (hereinafter referred to as "Benzophenone A").

The herbicidal compounds can be, for example, compounds which possess a high herbicidal activity within a wide concentration range and/or at low dosages, and may be used in agriculture, in particular for the selective control of undesired plants such as Alopecurus myosuroides, Echinochloa crus-galli, Setaria viridis, Galium aparine, Stellaria media, Veronica persica, Lamium purpureum, Viola arvensis, Abutilon theophrasti, Ipomoea purpurea and Amaranthus retroflexus by pre- and post-emergence application, particularly in certain crops such as maize and rice.

Preferred herbicides are the water-insoluble compounds selected from the group consisting of:
2,4-D, 2,4-DB, 2,4-DP, acetochlor, acifluorfen, alachlor, alloxydim, ametrydione, amidosulfuron, asulam, atrazin, azimsulfuron, benfuresate, bensulfuron, bentazon, bifenox, bromobutide, bromoxynil, butachlor, cafenstrole, carfentrazone, chloridazon, chlorimuron, chlorpropham, chlorsulfuron, chlortoluron, cinmethylin, cinosulfuron, clomazone, clopyralid, cyanazin, cycloate, cyclosulfamuron, cycloxydim, daimuron, desmedipham, di-methazone, dicamba, dichlobenil, diclofop, diflufenican, dimethenamid, dithiopyr, diuron, eptame, esprocarb, ethiozin, fenoxaprop, flamprop-M-isopropyl, flamprop-M-methyl, fluazifop, fluometuron, fluoroglycofen, fluridone, fluroxypyr, flurtamone, fluthiamid, fomesafen, glyphosate, halosafen, haloxyfop, hexazinone, imazamethapyr, imazamox, imazapyr, imazaquin, imazethapyr, ioxynil, isoproturon, isoxaben, isoxaflutole, lactofen, MCPA, MCPP, mefenacet, metabenzthiazuron, metamitron, metazachlor, methyldimron, metolachlor, metribuzin, metsulfuron, molinate, nicosulfuron, norflurazon, oryzalin, oxadiargyl, oxasulfuron, oxyfluorfen, pendimethalin, picloram, picolinafen, pretilachlor, propachlor, propanil, prosulfocarb, pyrazosulfuron, pyridate, qinmerac, quinchlorac, quizalofopethyl, sethoxydim, simetryne, sulcotrione, sulfentrazone, sulfosate, terbutryne, terbutylazin, thiameturon, thifensulfuron, thiobencarb, tralkoxydim, triallate, triasulfuron, tribenuron, triclopyr, trifluralin, and in particular pendimethalin.

Mixtures of the above mentioned herbicides or mixtures of herbicides with other active ingredients like fungicides, insecticides, acaricides, and nematicides are possible.

These herbicidal compounds are mostly known from "The Pesticide Manual".

Suitable adjuvants (b) are selected from the group consisting of alcohol alkoxylates and water-immiscible N-alkyl-pyrrolidones, preferably N-$C_{3-15}$ alkyl-pyrrolidones, in particular N-octyl-pyrrolidone or N-dodecyl-pyrrolidone.

A preferred alcohol alkoxylate is based on alkoxy units having 2 carbon atoms, thus being a mixed ethoxylate, or 2 and 3 carbon atoms, thus being a mixed ethoxylate/propoxylate. In a preferred aliphatic alcohol alkoxylate, the alkoxylate chain may have at least 5 alkoxy moieties, suitably from 5 to 25 alkoxy moieties, preferably 5 to 15, in particular 5 to 11. The alcohol moiety is as a rule derived from a $C_{9-18}$ aliphatic alcohol. Preferred alcohols are typically 50% by weight straight-chained and 50% by weight branched alcohols.

Particularly preferred are Neodol® (formerly Dobanol®) alcohol ethoxylates from Shell Chemical Co. Ltd. and Synperonic® alcohol ethoxylates from Uniqema (formerly ICI Surfactants), in particular Synperonic® 91-6.

Furthermore preferred alcohol alkoxylates are mono-branched alcohol ethoxylates such as Atplus® MBA 11-7 (branched $C_{11}$ alcohol ethoxylate with 7 ethoxy units) of Uniqema or Genapol® X-60 ($C_{13}$ alcohol ethoxylate with 6 ethoxy units) of Clariant GmbH.

In a particularly preferred embodiment of the present invention the adjuvant (b) of the inventive EC formulations comprises both one alcohol alkoxylate, in particular Synperonic® 91-6 or Atplus® MBA 11-7 and one water-immiscible N-alkyl-pyrrolidone, in particular N-octyl-pyrrolidone or N-dodecyl-pyrrolidone.

In the preferred ECs according to the present invention, wherein the adjuvant (b) consists of both one alcohol alkoxylate and one water-immiscible N-alkyl-pyrrolidone, the emulsifying surfactant system may consist of one or more non-ionic surfactants only.

Suitable organic solvents wherein the pesticide has to be dissolved are as a rule water-immiscible solvents. They are preferably selected from the group consisting of aromatic hydrocarbons, aliphatic hydrocarbons, dialkylene glycol dialkyl ethers and esters of plant oils or mixtures thereof.

Aromatic and aliphatic hydrocarbons such as hexane, cyclohexane, benzene, toluene, xylene, mineral oil or kerosin or substituted naphthalenes, mixtures of mono- and polyalkylated aromatics are commercially available under the registered trademarks Solvesso® and Shellsol® and Petrol Spezial®.

Esters of plant oils, which are used as nonpolar, water immiscible solvents according to the present invention, are as a rule alkyl esters obtainable from medium chained fatty acids by esterification with alkanols or by transesterification of the corresponding plant oils preferably in the presence of a lipase. Preferred fatty acids of these plant oils have 5 to 20, in particular 6 to 15 carbon atoms. As a rule they are mixtures of fatty acids having different chain lengths, mixtures in which the main component, i.e. more than 50 percent of said mixture, has 8 or 10 carbon atoms are particularly preferred. In a preferred embodiment the methyl ester of the plant oil used is the methyl ester of caprylic/capric ester or of capric ester having less than 5 percent of fatty acids having chain lengths different from 10.

Particularly preferred methyl esters of plant oils are Witconol® 1095 and Witconol® 2309 which are commercially available from the Witco Corporation, Houston, Tex., USA.

The water-miscible polar aprotic co-solvents used as cosolvents are necessary to increase the amount of the active ingredient and the adjuvant in the EC formulation. Without these co-solvents relatively small amounts of the active ingredient and of the adjuvant are soluble in the EC and the resulting formulation may show phytotoxicity due to the increased amount of solvent applied to the plant at a certain application rate of the active ingredient. Preferred polar solvents are compounds which exhibit a dielectric constant of 2.5 or more at 25° C., in particular from 2.7 to 4.0 at 25° C. Preferred are alcohols such as benzyl alcohol, ketones, alkylene carbonates such as ethylene carbonate and propylene carbonate, amides, in particular cyclic amides and lactones as for example N-methylpyrrolidone, γ-butyrolactone, N-cyclohexyl-pyrrolidone, and cyclohexanone. Most preferred are γ-butyrolactone and N-cyclohexyl-pyrrolidone.

In another preferred embodiment of the invention the co-solvent consists essentially of one or more, preferably 2 or 3 dimethyl dicarboxylates of formula

wherein n is 2, 3 or 4.

Particularly preferred is a mixture consisting of glutaric acid dimethyl ester, succinic acid dimethyl ester and adipic acid dimethyl ester, most preferred DBE, which is available from Lemro Chemieprodukte Michael Mrozyk KG, Grevenbroich, Germany.

The emulsifying surfactant system enabling the EC to form an oil in water emulsion when the formulation is added to water is a mixture of two or more surfactants, at least one of which is a nonionic surfactant and optionally at least one of which is an anionic surfactant.

Suitable anionic surfactants may be so-called water-soluble soaps as well as synthetic surface-active compounds. Soaps usually are alkali, earth alkali or optionally substituted ammonium salts of higher fatty acids ($C_{10}$–$C_{20}$), e.g. the sodium or potassium salts of oleic or stearic acid or of mixtures of natural fatty acids which are prepared, for example, from coconut or tallow oil. Furthermore, methyl-taurine salts of fatty acids may be used. However, so-called synthetic surfactants are preferably used, especially fatty sulfonates, fatty sulfates, sulfonated benzimidazole derivatives or alkyl aryl sulfonates. The fatty sulfates or fatty sulfonates are normally used as alkali, earth alkali or optionally substituted ammonium salts and have an alkyl moiety of 8 to 22 carbon atoms, whereby alkyl also means the alkyl moiety of acyl residues, such as the sodium or calcium salt of lignin sulfonic acid, of sulfuric acid dodecylate or of a mixture of fatty alcohols prepared from natural fatty acids. This also includes the salts of sulfuric acid esters, sulfonic acids and adducts of fatty alcohols and ethylene oxide. The sulfonated benzimidazole derivatives preferably contain 2 sulfonic acid residues and a fatty acid residue with 8 to 22 carbon atoms. Alkyl aryl sulfonates are, for example, the sodium, calcium or triethyl ammonium salts of dodecyl benzene sulfonic acid, dibutyl naphthalene sulfonic acid or of a condensate of naphthalene sulfonic acid and formaldehyde. Furthermore, phosphates, such as the salts of the phosphoric acid ester of a p-nonylphenol-(4-14)-ethylene oxide adduct or phospholipids, may be used. Most preferred anionic surfactants are the sodium, calcium or triethyl ammonium salts of dodecyl benzene sulfonic acid, in particular Sponto® AD11-1A (a mixture of dodecyl benzene sulfonate, an alkyl ethoxylate and isobutanol) of Witco SA, Saint-Pierre les Elbeuf, France, Rhodocal® 70/B (70% linear dodecyl benzene sulfonate in n-butanol) and Rhodocal® 2283 (ammonium dodecyl benzene sulfonate) both of Rhodia GmbH (formerly Rhône-Poulenc), Phenyl-sulfonat CA 100 (40% branched calcium linear dodecyl benzene sulfonate in Genopol X-060 and Solvesso 200) of Clariant GmbH (formerly Hoechst AG) or Nansa® EVM 70/2E (57% linear dodecyl benzene sulfonate in 2-ethylhexanol) of Albright & Wilson.

Non-ionic surfactants are preferably polyglycolether derivatives of aliphatic or cycloaliphatic alcohols, saturated or non-saturated fatty acids and alkylphenols, which have 3 to 10 glycol ether groups and 8 to 20 carbon atoms in the (aliphatic) hydrocarbon residue and 6 to 18 carbon atoms in the alkyl residue of the alkyl phenols. Other suitable non-ionic surfactants are the water-soluble, 20 to 250 ethylene glycol ether groups containing polyadducts of ethylene oxide and propylene oxide, ethylene diamino polypropylene glycol and alkyl polypropylene glycol with 1 to 10 carbon atoms in the alkyl moiety, the substances normally contain 1 to 5 ethylene glycol units per propylene glycol unit. Examples of non-ionic surfactants are nonylphenol polyethoxy ethanols, castor oil polyglycol ethers, polyadducts of ethylene oxide and propylene oxide, tributyl phenoxy polyethoxy ethanol, octyl phenoxy polyethoxy ethanol. Preferred are fatty acid esters of polyoxy ethylene sorbitan, such as polyoxy ethylene sorbitan trioleate, in particular Witconol® AL69-66 of Witco SA, Saint-Pierre les Elbeuf, France.

Further preferred are ethoxylated fatty acids such a castor or canola oil ethoxylates having at least 25, preferably 27 to 37 ethoxy units, such as Sunaptol® CA350 (castor oil ethoxylate with 35 ethoxy units) of ICI surfactants, Mergital® EL33 (castor oil ethoxylate with 33 ethoxy units) of Henkel KGaA, Eumulgin® C03373 (canola oil ethoxylate with 30 ethoxy units) of Henkel KGaA and Ukanil® 2507 (castor oil ethoxylate) of Uniqema.

As a rule, the surfactant system according to the present invention consists of one anionic surfactant and one or two non-ionic surfactants, preferably one of the non-ionic surfactants is a castor oil ethoxylate.

These materials provide good emulsifying properties without containing alkylphenol ethoxylates, such as Synperonic® NP9 and/or the anionic derivatives thereof for example ethoxylated alkylaryl phosphate esters such as Rhodofac® RE 610. Alkylphenol ethoxylates and their derivatives may damage the environment due to their foaming behavior and possible oestrogenic activity.

The surfactants generally used for compositions of the invention are disclosed in publications such as:

"McCutheon's Detergents and Emulsifiers Annual", MC Publishing Corp., Ridgewood, N.J., USA 1981;

H. Stache, "Tensid-Taschenbuch", 2nd ed., C. Hanser, Munich, Vienna, 1981;

M. and J. Ash, "Encyclopedia of Surfactants", Vol. I—III, Chemical Publishing Co., New York, N.Y., USA 1980–1981.

Specific embodiments of the invention are as follows:

(i) An EC containing
  100 to 350 g/l of one or more crop protection active compounds;
  150 to 500 g/l of one or more adjuvants;
  up to 400 g/l, preferably 150 to 400 g/l of one or more organic solvents;
  20 to 150 g/l of the said emulsifying surfactant system,
  80 to 300 g/l of the said water-miscible polar aprotic solvent, or 100 to 300 g/l of one or more dimethyl dicarboxylates,
  0.1 to 20 g/l of one or more antifoam agents,
wherein the sum of all ingredients in the EC adds up to one liter.

(ii) An EC consisting essentially of
  100 to 350 g/l, in particular 120 to 300 g/l of one or more herbicides or fungicides;
  150 to 500 g/l, in particular 175 to 400 g/l of one or more adjuvants; selected from the group consisting of alcohol alkoxylates and water-immiscible N-alkylpyrrolidones,
  up to 400 g/l, in particular 175 to 350 g/l of one or more organic solvents selected from the group consisting of aromatic hydrocarbons, aliphatic hydrocarbons, diethylene glycol dialkyl ethers and esters of plant oils or mixtures thereof,
  20 to 150 g/l, in particular 50 to 120 g/l of the said emulsifying surfactant system consisting of one anionic surfactant and one non-ionic surfactant,
  80 to 300 g/l of the said water-miscible polar aprotic solvent, or 100 to 300 g/l of one or more dimethyl dicarboxylates, and
  0.1 to 20 g/l of one or more antifoam agents.

The solubility of the active ingredients in the formulation according to the invention depends not only on the structure of the active ingredient but also on the amount of the cosolvent. The relative amount of active ingredient soluble in the EC (a) increases by about 40 to 60% when 10 to 15% cosolvent (e) is incorporated into the formulation.

Another aspect of the invention is a process for the preparation of an EC as described hereinbefore, which comprises mixing all the components (a) to (f) in a dissolver.

Furthermore, the invention relates to a method of combating pests at a locus which comprises treating the locus with a composition obtained from emulsifying an EC according to the invention in water.

Moreover, the invention relates to the use of an EC according to the invention as a pesticide.

As commodities, the inventive pesticidal ECs may preferably be in a concentrated form whereas the end-user generally employs diluted compositions. Said compositions may be diluted to concentrations down to 0.001% of active ingredient (a.i.). The doses usually are in the range of about 0.01 to 10 kg a.i./ha.

These compositions may also comprise other auxiliaries such as chemical stabilizers, viscosity controlling agents, thickeners, adhesives, fertilizers, anti-foam agents or other active pesticide ingredients to obtain special effects.

Preferred anti-foam agents are silica, polydialkylsiloxanes, in particular polydimethylsiloxanes such as Rhodorsil® 416 or Rhodosil® 454 from Rhône Poulenc, fluoroaliphatic esters such as Fluorad® FC-430 from 3M or perfluoroalkylphosphonic/perfluoroalkylphosphonic acids or the salts thereof such as Fluowet® PL80, Fluowet PP or Defoamer SF from Clariant and mixtures thereof. Particularly preferred is a combination of polydimethylsiloxanes and perfluoroalkylphosphonic/perfluoroalkylphosphinc acids.

For a clearer understanding of the invention, specific examples are set forth below. These examples are merely illustrations and are not to be understood as limiting the scope and underlying principles of the invention in any way. Indeed, various modifications of the invention in addition to those shown and described herein will become apparent to those skilled in the art from the following examples and foregoing description. Such modifications are also intended to fall within the scope of the appended claims.

PREPARATION EXAMPLES

The registered trademarks and other designations denote the following products:

| Ingredient | Composition | Manufacturer |
| --- | --- | --- |
| Synperonic ® 91-6 | Alcohol ethoxylate | Uniqema |
| Solventnaphtha | Aromatic hydrocarbon mixture | Shell |
| Shellsol A | Aromatic hydrocarbon mixture | Shell |
| Solvesso 200 | Aromatic hydrocarbon mixture | Esso |
| Atplus ® MBA 11-7 | Monobranched alcohol ethoxylate | Uniqema |
| Atplus ® 4855B | Calcium alkylarylsulfonate, nonionic blend in an aromatic solvent | Uniqema |
| Atlox ® 3300B | Isopropylamine dodecyl benzene sulfonate | Uniqema |

-continued

| Ingredient | Composition | Manufacturer |
|---|---|---|
| Rhodocal ® 70/B | 70% Calcium dodecyl benzene sulfonate and 30% butanol | Rhône-Poulenc |
| Rhodocal ® 2283 | Amine salt of dodecyl benzene sulfonate in an aromatic solvent | Rhône-Poulenc |
| Ukanil ® 2507 | Castor oil ethoxylate | Uniqema |
| Fluowet ® PL80 | 80% Mixture of perfluorinated phophinic/phosphoric acids; 20% Water | Clariant |
| Fluowet ® PP | Mixture of perfluorinated phophinic/phosphoric adds | Clariant |
| CHP | Cyclohexylpyrrolidone | ISP |
| Agrimer ® AL25 | Mixture of 55% vinylpyrrdidone co-polymer, 50% $C_{16}$ alkylated, and 45% isopropanol | ISP |
| Eumulgin ® CO3373 | Canola oil, ethoxylated, 30 EO units | Henkel KGaA |
| Phenylsulfonat CA 100 | Mixture of calcium salt of branched dodecyl benzene sulfonate, Genopol X-060, and Solvesso 200 | Clariant GmbH |
| Rhodorsil ® 416 | Mixture of polydimethylsiloxanes, silica, and a nonionic surfactant | Rhône-Poulenc |
| Rhodorsil ® 454 | Mixture of polydimethylsiloxanes and silica | Rhône-Poulenc |
| Fluorad ® FC-430 | Mixture of fluoroaliphatic esters | 3M |
| Agsol Ex8 | N-octylpyrrolidone | ISP |
| Agsol Ex12 | N-dodecylpyrrolidone | ISP |
| DBE | Mixture of 59% glutaric acid dimethyl ester, 20% succinic acid dimethyl ester and 21% adipic acid dimethyl ester | Lemro Chemie-Produkte KG, Grevenbroich, Germany |
| Mergital EL33 | Castor oil ethoxylate with 33 EO units | Henkel |

All ingredients are weighed into a container and stirred until a homogenous solution is obtained.

Examples 1 to 5

An EC formulation is prepared containing:

| Ingredient | Example 1 | Example 2 | Example 3 | Example 4 | Example 5 |
|---|---|---|---|---|---|
| Benzoylbenzene A | 175 g | 150 g | 150 g | 150 g | 150 g |
| Rhodocal 2283 | 50 g | — | — | — | — |
| Rhodocal 70/B | — | 50 g | 50 g | 20 g | 20 g |
| Ukanil 2507 | 50 g | 30 g | 30 g | 50 g | 50 g |
| Synperonic 91-6 | — | 200 g | — | 330 g | 250 g |
| Atplus MBA 11-7 | — | — | 200 g | — | — |
| Agsol Ex8 | 240 g | 150 g | 150 g | — | — |
| γ-Butyrolactone | 240 g | 200 g | 200 g | 100 g | 200 g |
| Fluowet PL80 | — | 0.5 g | — | — | — |
| Solventnaphtha | to 1 liter | to 1 liter | to 1 liter | 100 g | 100 g |
| Diethylene glycol dimethyl ether | — | — | — | to 1 liter | — |
| Diethylene glycol diethyl ether | — | — | — | — | to 1 liter |

The resulting formulation exhibit the following physico-chemical properties

| Property | Example 1 | Example 2 | Example 3 | Example 4 | Example 5 |
|---|---|---|---|---|---|
| Density | 1.02 g/ml | 1.02 g/ml | 1.02 g/ml | 1.03 g/ml | 1.01 g/ml |
| Flash point | 54° C. | 54° C. | 61° C. | 56° C. | 52° C. |
| Storage of | no | no | no | no | no |
| EC for 7 days ° C. | crystals, solution clear | crystals, solution clear | crystals, solution clear | crystals, solution clear | crystals, solution clear |

Example 6

An EC formulation is prepared containing:

| Ingredient | Concentration |
|---|---|
| Dimethomorph | 30 g/L |
| Phenylsulfonat CA100 | 50 g/L |
| Emulgin CO3373 | 50 g/L |
| MBA 11-7 | 218 g/L |
| γ-Butyrolactone | 218 g/L |
| Fluowet PP | 0.5 g/L |
| Agsol Ex12 | to 1 L |
| Density | 0.99 g/mL |

Example 7

An EC formulation is prepared containing:

| Ingredient | Concentration |
|---|---|
| Dimethomorph | 35 g/L |
| Phenylsulfonat CA100 | 20 g/L |
| Emulgin CO3373 | 80 g/L |
| Synperonic 91-6 | 217 g/L |
| γ-Butyrolactone | 217 g/L |
| Solvesso 200 | 217 g/L |
| Fluowet PP | 0.5 g/L |
| Agsol Ex12 | to 1 L |
| Density | 1.01 g/mL |

Example 8

An EC formulation is prepared containing:

| Ingredient | Concentration |
|---|---|
| Dimethomorph | 30 g/L |
| Phenylsulfonat CA100 | 80 g/L |
| Emulgin CO3373 | 20 g/L |
| Synperonic 91-6 | 348 g/L |

| Ingredient | Concentration |
|---|---|
| DBE | 261 g/L |
| Rhodorsil 416 | 1 g/L |
| Agsol Ex12 | to 1 L |
| Density | 1.00 g/mL |

Example 9

An EC formulation is prepared containing:

| Ingredient | Concentration |
|---|---|
| Metconazole | 180 g/L |
| Atplus 4855B | 100 g/l |
| Synperonic 91-6 | 180 g/L |
| Solvesso 200 | 180 g/L |
| CHP | 180 g/L |
| Rhodorsil 454 | 1 g/L |
| Agsol Ex8 | to 1 L |
| Density | 1.02 g/mL |

Example 10

An EC formulation is prepared containing:

| Ingredient | Concentration |
|---|---|
| Metconazole | 160 g/L |
| Atplus 4855B | 100 g/l |
| Synperonic 91-6 | 296 g/L |
| DBE | 222 g/L |
| Rhodorsil 454 | 1.0 g/L |
| Agsol Ex12 | to 1 L |
| Density | 1.03 g/mL |

Example 11

An EC formulation is prepared containing:

| Ingredient | Concentration |
|---|---|
| Metconazole | 160 g/L |
| Atplus 4855B | 100 g/L |
| Atplus 871 | 296 g/L |
| DBE | 222 g/L |
| Rhodorsil 454 | 1.0 g/L |
| Agsol Ex12 | to 1 L |
| Density | 1.03 g/mL |

Example 12

An EC formulation is prepared containing:

| Ingredient | Concentration |
|---|---|
| Pendimethalin | 330 g/L |
| Phenylsulfonat CA100 | 80 g/L |
| Ukanil 2507 | 20 g/L |
| Synperonic 91-6 | 285 g/L |
| γ-Butyrolactone | 145 g/L |
| Solvesso 200 | 145 g/L |
| Fluorad FC-430 | 0.5 g/L |
| Agsol Ex12 | to 1 L |
| Density | 1.04 g/mL |

Example 13

An EC formulation is prepared containing:

| Ingredient | Concentration |
|---|---|
| Pendimethalin | 300 g/L |
| Phenylsulfonat CA100 | 20 g/L |
| Ukanil 2507 | 80 g/L |
| Synperonic 91-6 | 150 g/L |
| Solvesso 200 | 225 g/L |
| Fluorad FC-430 | 0.5 g/L |
| Agsol Ex12 | to 1 L |
| Density | 1.02 g/mL |

Example 14

An EC formulation is prepared containing:

| Ingredient | Concentration |
|---|---|
| Pendimethalin | 240 g/L |
| Phenylsulfonat CA100 | 50 g/L |
| Ukanil 2507 | 50 g/L |
| Synperonic 91-6 | 264 g/L |
| DBE | 198 g/L |
| Fluowet PP | 1 g/L |
| Agsol Ex12 | to 1 L |
| Density | 1.02 g/mL |

Example 15

An EC formulation is prepared containing:

| Ingredient | Concentration |
|---|---|
| Pendimethalin | 240 g/L |
| Phenylsulfonat CA100 | 50 g/L |
| Ukanil 2507 | 50 g/L |
| Synperonic 91-6 | 330 g/L |
| Solventnaphtha | 165 g/L |
| Fluowet PP | 1 g/L |
| Agsol Ex12 | to 1 L |
| Density | 1.01 g/mL |

Example 16

An EC formulation is prepared containing:

| Ingredient | Concentration |
|---|---|
| Pendimethalin | 330 g/L |
| Phenylsulfonat CA100 | 50 g/L |
| Ukanil 2507 | 50 g/L |
| Synperonic 91-6 | 285 g/L |
| Fluowet PP | 1 g/L |
| Agsol Ex12 | to 1 L |
| Density | 1.01 g/mL |

Example 17

An EC formulation is prepared containing:

| Ingredient | Concentration |
| --- | --- |
| Metconazole | 90 g/L |
| Benzoylbenzene A | 100 g/L |
| Synperonic 91-6 | 300 g/L |
| Phenylsulfonat CA100 | 30 g/L |
| Mergital EL33 | 60 g/L |
| Fluowet PL80 | 0.5 g/L |
| Rhodorsil 454 | 0.2 g/L |
| Solventnaphtha | 175 g/L |
| Butyrolactone | 170 g/L |
| Solvesso 200 | to 1 L |
| Density | 1.04 g/mL |

Example 18

An EC formulation is prepared containing:

| Ingredient | Concentration |
| --- | --- |
| Benzoylbenzene A | 150 g/L |
| Butyrolactone | 200 g/L |
| n-Octylpyrrolidone | 150 g/L |
| Synperonic 91-6 | 200 g/L |
| Phenylsulfonat CA100 | 87.5 g/L |
| Ukanil 2507 | 30 g/L |
| Fluoweg PL80 | 0.5 g/L |
| Solvesso 200 | 100 g/L |
| Solventnaphtha | to 1 L |
| Density | 1.04 g/mL |
| Flash point | 71° C. |

Example 19

An EC formulation is prepared containing:

| Ingredient | Concentration |
| --- | --- |
| Benzoylbenzene A | 150 g/L |
| Butyrolactone | 200 g/L |
| n-Octylpyrrolidone | 150 g/L |
| Synperonic 91-6 | 200 g/L |
| Rhodocal 70/B | 50 g/L |
| Ukanil 2507 | 30 g/L |
| Fluoweg PL80 | 0.5 g/L |
| Solventnaphtha | 240 g/L |
| Density | 1.02 g/mL |
| Flash point | 54° C. |

The new EC formulations are stable down to at least 0° C. and mostly to 5° C.

The new ECs are biologically very active (much more than ECs without an adjuvant). The adjuvants include n-octylpyrrolidone, n-dodecylpyrrolidone, Synperonic 91-6 and MBA 11-7. The spray dilutions (emulsions) are stable despite a high concentration of water miscible substances (Synperonic 91-6, γ-butyrolactone). The ingredients have a good environmental profile. In the past, adjuvants have typically been added to the spray tank separately from the pesticidal formulation ("tank-mix adjuvant"). The adjuvant in a one-pack formulation is easier to use than as a tank-mix adjuvant.

What is claimed is:

1. A stable emulsifiable concentrate formulation for the protection of agricultural crops which comprises
   (a) one or more crop protection active compounds;
   (b) 150 to 500 g/l of one or more adjuvants selected from the group consisting of an alcohol alkoxylate, a water-immiscible N-alkylpyrrolidone and a mixture thereof;
   (c) optionally one or more organic solvents;
   (d) an emulsifying surfactant system enabling an oil in water emulsion to be formed when the formulation is added to water, which comprises:
      one or more non-ionic surfactants and
      one or more anionic surfactants; and
   (e) one or more solvents selected from the group consisting of a water-miscible polar aprotic solvent and one or more dimethyl dicarboxylates.

2. The formulation according to claim 1 which comprises
   (a) 100 to 350 g/l of one or more crop protection active compounds;
   (b) 150 to 500 g/l of one or more adjuvants;
   (c) up to 400 g/l of one or more organic solvents;
   (d) 20 to 150 g/l of the emulsifying surfactant system,
   (e) 80 to 300 g/l of the solvent, and
   (f) 0.1 to 20 g/l of one or more antifoam agents,
wherein the sum of all ingredients in the suspension adds up to one liter.

3. The formulation according to claim 1 wherein said crop protection active compounds (a) are selected from the group consisting of herbicides, insecticides, fungicides, bactericides, nematicides, algicides, molluscicides, rodenticides, virucides, compounds inducing resistance into plants, biological control agents such as viruses, bacteria, nematodes, fungi and other microorganisms, repellents of birds and animals, and plant growth regulators, or mixtures thereof.

4. The formulation according to claim 3 wherein said crop protection active compound (a) is a fungicide.

5. The formulation according to claim 4 wherein said crop protection active compound (a) is a compound of formula I

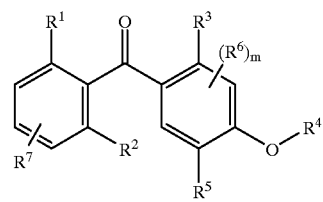

wherein
   $R^1$ represents a chloro atom or a methyl or trifluoromethyl group;
   $R^2$ represents a chloro atom or an alkyl, alkoxy or hydroxy group;
   $R^3$ represents a halogen atom, an optionally substituted alkyl, alkoxy, alkenyl, alkylthio, alkylsulfinyl, alkylsulfonyl, cyano, carboxy, hydroxy, nitro or an optionally substituted amino group;
   $R^4$ represents an optionally substituted alkyl group;
   $R^5$ represents an optionally substituted alkyl, alkoxy, alkenyloxy, alkynyloxy, alkylthio, cycloalkyl, cycloalkyloxy, group;
   m is an integer of 1 or 2;
   $R^6$ independently represents an optionally substituted alkoxy or alkanoyloxy group; and $R^7$ represents a hydrogen or halogen atom or an alkyl, haloalkyl or alkoxy group.

6. A method for the control of pests at a locus which comprises diluting an emulsifiable concentrate formulation as claimed in claim 1 with water and treating said locus with the obtained diluted formulation.

7. The formulation according to claim 1 wherein said water-immiscible N-alkylpyrrolidone is selected from the group consisting of N-octylpyrrolidone and N-dodecylpyrrolidone.

8. The formulation according to claim 1 wherein the solvent (c) is selected from the group consisting of aromatic hydrocarbons, aliphatic hydrocarbons, diethylene glycol dialkyl ethers and esters of plant oils or mixtures thereof.

9. The formulation according to claim 1 wherein the non-ionic surfactant (d) is selected from the group consisting of a polyoxyethylene fatty acid and an ethoxylated triglyceride.

10. The formulation according to claim 1 wherein the anionic surfactant (d) is selected from the group consisting of an alkali or earth alkali sulfonate.

11. The formulation according to claim 1 wherein said co-solvent (e) exhibits a dielectricity constant of at least 15 at 25° C.

12. The formulation according to claim 11 wherein said co-solvent (e) is selected from the group consisting of γ-butyrolactone, N-methylpyrrolidone, N-cyclohexylpyrrolidone, cyclohexanone, glutaric acid dimethyl ester, succinic acid dimethyl ester and adipic acid dimethyl ester.

13. The formulation according to claim 1 wherein said antifoam agent (f) is selected from the group consisting of silica, polydialkylsiloxanes, fluoroaliphatic esters and perfluoroalkylphosphonic/perfluoroalkylphosphinc acids or the salts thereof and mixtures thereof.

* * * * *